(12) United States Patent
Rao et al.

(10) Patent No.: US 8,987,458 B2
(45) Date of Patent: Mar. 24, 2015

(54) PROCESS FOR THE PREPARATION OF DONEPEZIL HYDROCHLORIDE

(75) Inventors: Dharmaraj Ramachandra Rao, Maharashtra (IN); Rajendra Narayanrao Kankan, Maharashtra (IN); Srinivas Laxminarayan Pathi, Karnataka (IN)

(73) Assignee: Cipla Limited, Mumbai (IN)

( * ) Notice: Subject to any disclaimer, the term of this patent is extended or adjusted under 35 U.S.C. 154(b) by 401 days.

(21) Appl. No.: 12/934,245

(22) PCT Filed: Mar. 24, 2009

(86) PCT No.: PCT/GB2009/000776
§ 371 (c)(1),
(2), (4) Date: Dec. 13, 2010

(87) PCT Pub. No.: WO2009/118516
PCT Pub. Date: Oct. 1, 2009

(65) Prior Publication Data
US 2011/0077271 A1    Mar. 31, 2011

(30) Foreign Application Priority Data
Mar. 25, 2008    (IN) ............................ 636/MUM/2008

(51) Int. Cl.
C07D 211/02    (2006.01)
C07D 213/20    (2006.01)
C07D 211/32    (2006.01)

(52) U.S. Cl.
CPC ............ C07D 213/20 (2013.01); C07D 211/32 (2013.01)
USPC .......................................... 546/206; 546/205

(58) Field of Classification Search
CPC ........................... C07D 211/02; C07D 213/20
USPC .................... 546/205, 206, 238, 342
See application file for complete search history.

(56) References Cited

U.S. PATENT DOCUMENTS

| | | | |
|---|---|---|---|
| 2,906,699 A * | 9/1959 | Haensel et al. | 208/138 |
| 4,895,841 A | 1/1990 | Sugimoto et al. | |
| 5,606,064 A | 2/1997 | Lensky | |
| 6,252,081 B1 | 6/2001 | Iimura | |
| 6,649,765 B1 | 11/2003 | Vidyadhar et al. | |
| 6,953,856 B2 | 10/2005 | Radhakrishnan et al. | |
| 8,124,783 B2 * | 2/2012 | Dubey et al. | 546/342 |
| 2007/0135644 A1 | 6/2007 | Pospisilik | |

FOREIGN PATENT DOCUMENTS

| | | | |
|---|---|---|---|
| WO | WO0002081 | * | 1/2002 |
| WO | 2004082685 A1 | | 9/2004 |
| WO | 2008010235 A2 | | 1/2008 |
| WO | 2009118516 A1 | | 10/2009 |
| WO | 2009118516 A8 | | 10/2009 |

OTHER PUBLICATIONS

DonepezilHCl "product description" Biotang p. 1 (2013).*
DonepezilHCI "Product description" China Org. Intermediate p. 1 (2013).*
Salt "Chemistry definition", Wikipedia, p. 1-3 (2013).*
"Ionic compound" p. 1 Wikipedia (2013).*
Sajiki et al. "Pd/C-catalyzed . . . " Chem. Pharm. Bull. 54(3) 320-324 (2003).*
Johnson Matthey "catalyst" p. 1-2 (2008).*
Foreign communication from the priority application—International Preliminary Report on Patentability, PCT/GB2009/000776, Sep. 28, 2010, 10 pages.
Foreign communication from the priority application—International Search Report and Written Opinion, PCT/GB2009/000776, Jun. 30, 2009, 13 pages.

* cited by examiner

*Primary Examiner* — Celia Chang
(74) *Attorney, Agent, or Firm* — Conley Rose, P.C.; Rodney B. Carroll

(57) ABSTRACT

The present invention provides a process for preparing donepezil or a salt thereof, the process comprising reducing a 1-benzyl-4-[(5,6-dimethoxy-1-indanon-2-yl)methylene]pyridonium halide of formula II, wherein X is bromide or chloride, in the presence of an ionic compound, a solvent, a catalyst and a source of hydrogen, to form donepezil and optionally converting the donepezil to the salt thereof.

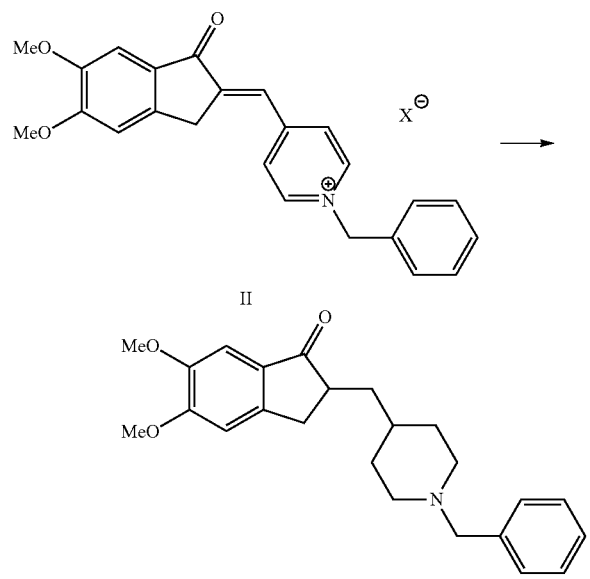

17 Claims, No Drawings

PROCESS FOR THE PREPARATION OF DONEPEZIL HYDROCHLORIDE

CROSS-REFERENCE TO RELATED APPLICATIONS

This application is a filing under 35 U.S.C. 371 of International Application No. PCT/GB2009/000776 filed Mar. 24, 2009, entitled "Process for the Preparation of Donepezil Hydrochloride," claiming priority of Indian Patent Application No. 636/MUM/2008 filed Mar. 25, 2008, which applications are incorporated by reference herein in their entirety.

FIELD OF INVENTION

The present invention relates to an improved process for the preparation of highly pure donepezil hydrochloride. More, particularly, the present invention relates to an improved process for the preparation of donepezil hydrochloride using a novel reduction step carried out using at least one hydrogenation catalyst, in the presence of ionic compounds in organic solvents or an aqueous solvent or mixture thereof from 1-benzyl-4-[5,6-dimethoxy-1-indanon-2-yl)methylene]pyridonium bromide. More particularly, the invention relates to an industrially suitable process for the preparation of donepezil hydrochloride.

BACKGROUND OF THE INVENTION

Donepezil hydrochloride, which is chemically known as 1-benzyl-4-[(5,6-dimethoxy-1-indanon)-2-yl)methyl piperidine hydrochloride [formula I]

Formula I

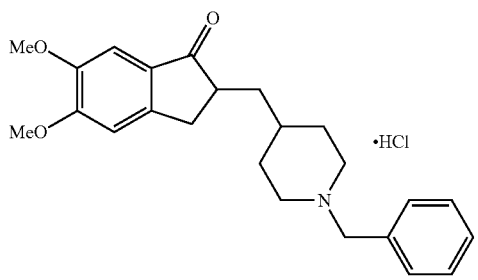

is used in the treatment of Alzheimer's disease where it is used to increase cortical acetylcholine. It is available for oral administration in film-coated tablets containing 5 or 10 mg of donepezil hydrochloride.

Donepezil hydrochloride is well known in the art and was first disclosed in U.S. Pat. No. 4,895,841, hereinafter referred to as the '841 patent. As described therein, donepezil hydrochloride is prepared by reacting 5,6-dimethoxy-1-indanone with 1-benzyl-4-formylpiperidine in the presence of a strong base such as lithium diisopropyl amide followed by a reduction step (Examples 3 and 4) with a palladium carbon catalyst in tetrahydrofuran (THF). The residue was purified by making use of silica gel column chromatography. This process, however, suffers from certain evident limitations. The procedure laid down for reduction of 1-benzyl-4-[(5,6-dimethoxy-1-indanon)-2-ylidenyl]methyl piperidine is not industrially feasible. It entails the use of column chromatography for the purification of the hydrogenated residue, which cannot be carried out industrially. Further, the process makes use of THF, which is a highly flammable solvent and may form explosive peroxide vapors. Moreover, the overall yield of donepezil HCl is reported to be 50.8%. The purity of the product obtained is not disclosed in the patent.

U.S. Pat. No. 5,606,064, hereinafter referred to as the '064 patent, and U.S. Pat. No. 6,252,081 describe a process for the preparation of donepezil wherein 1-benzyl-4-(5,6-dimethoxyindan-1-on-2-ylidene)methyl pyridinium salt is reduced to yield donepezil. The reduction of the olefinic bond and a pyridinium ring in the presence of a benzyl group is difficult to achieve under the conditions disclosed in the patent. Further, the reaction requires at least 24 hours to complete (Example 6).

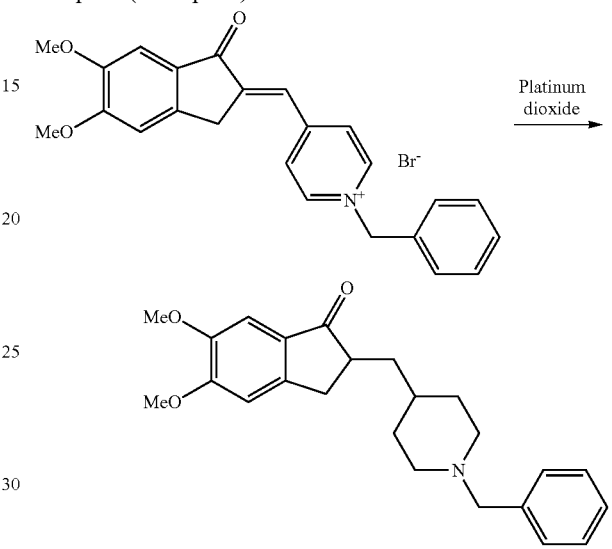

The major disadvantage of the process is that the reaction is carried out in the presence of methanol and platinum dioxide. The use of an expensive catalyst is not viable industrially. Moreover, on repeating the above process, unwanted side products are produced, such as a partly hydrogenated impurity of formula III Formula III

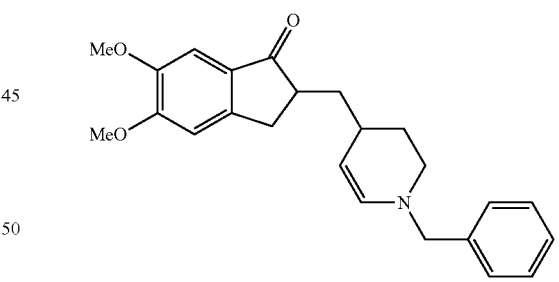

which is formed to an extent of 5%. This impurity is difficult to separate in the final crystallization, hence requires purification by column chromatography/repeated purification resulting in poor yield, hence making the process not feasible on an industrial scale. These impurities also affect the overall yield of the final product. Further, the purity of the product obtained is not disclosed in the patent.

U.S. Pat. No. 6,649,765 and US Patent Application published under no. 2004/0158070A1 describe the reduction of 5,6-dimethoxy-2-(pyridin-4-yl)methylene-indan-1-one using a noble metal oxide catalyst (platinum oxide) in a mixture of solvents such as acetic acid and methanol at 10-45 psi gauge pressure followed by benzylation to obtain donepezil hydrochloride. Besides making the process expensive, it is not industrially viable. Further, the purity of the product obtained is not disclosed in these patents.

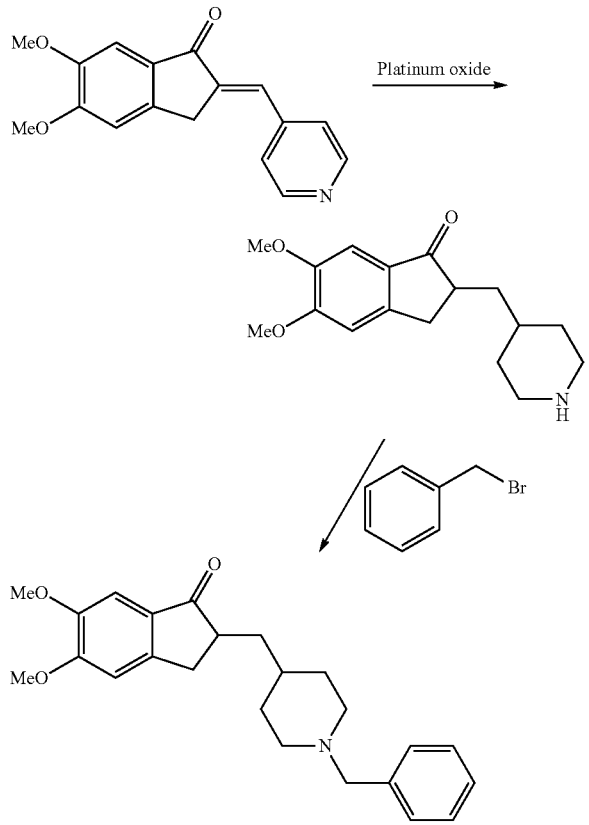

PCT Publication No. WO2004/082685 describes the preparation of donepezil which comprises a two-step reduction starting from 5,6-dimethoxy-2-(pyridine-4-yl)methylene-indan-1-one via the preparation of intermediate 5,6-dimethoxy-2-(4-pyridyl)methyl-indan-1-one using methanol as one of the solvents followed by benzylation.

The above process is also time consuming and difficult to carry out as it involves multiple steps.

US Patent Application published under the No. 2007/0135644A1 discloses the preparation of donepezil hydrochloride by reducing 5,6-dimethoxy-2-[1-(4-pyridinyl)methylidene]-1-indanone tosylate with 10% Pd/C catalyst in demi-water at 70-95° C., at 10 bar for 8 hours. The mixture is extracted three times with 1-butanol to afford a residue which is purified with methyl-tert-butyl ether to obtain 5,6-dimethoxy-2-(4-piperidinylmethyl)-1-indanone, followed by condensation with benzyl chloride in toluene for 8 hours at 145° C. to yield donepezil which is further converted to donepezil hydrochloride.

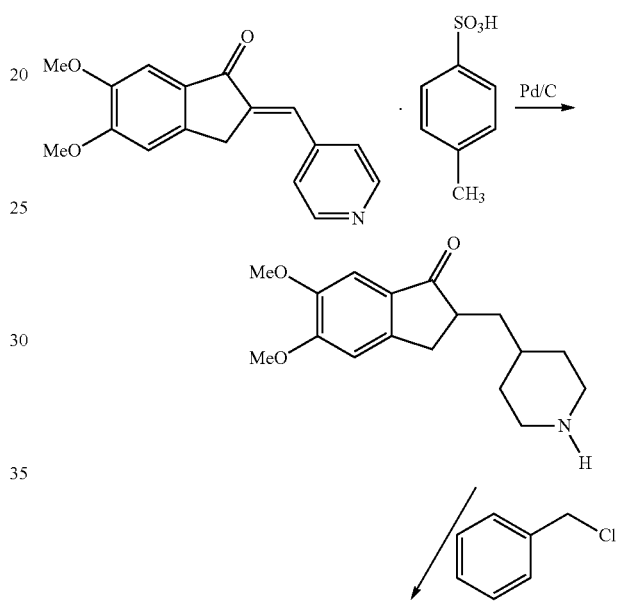

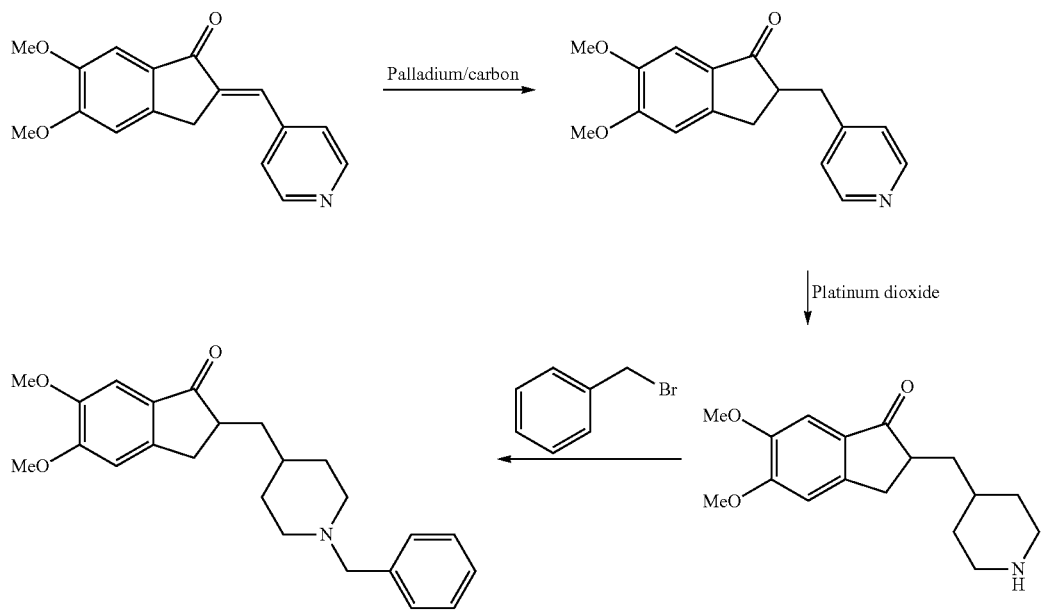 [SMILES: COc1cc2c(cc1OC)C(=O)/C(=C/c1ccncc1)C2 ; COc1cc2c(cc1OC)C(=O)C(Cc1ccncc1)C2 ; COc1cc2c(cc1OC)C(=O)C(CC1CCN(Cc3ccccc3)CC1)C2 ; BrCc1ccccc1 ; COc1cc2c(cc1OC)C(=O)C(CC1CCNCC1)C2]

-continued

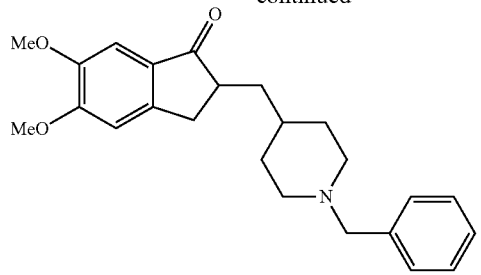

This process involves reduction at a high pressure of 10 bar and temperature of 70-95° C. which leads to impurities. Further, the benzylation reaction requires a high temperature of 145° C. for 8 hours. The work-up process is very lengthy thereby making the whole process industrially unfavorable.

PCT Publication No. WO 2008/010235 discloses a method for preparation of donepezil hydrochloride wherein 1-benzyl-4-[(5,6-dimethoxy-1-indanon)-2-ylidenyl]methyl piperidine, is reduced with metal borohydride in the presence of a catalytic amount of a cobalt salt in a large volume of THF as solvent to yield donepezil hydrochloride. This process is not viable industrially due to use of costly cobalt catalyst.

The prior art procedures for the preparation of donepezil have certain disadvantages, such as multiple reduction steps, and/or chromatographic separation of intermediates, side-product formation, giving low yields. These properties hinder the large-scale production of donepezil hydrochloride.

Therefore, there is a need to develop an industrially feasible, cost effective and environmentally friendly process for the preparation of donepezil hydrochloride of formula (I) with high purity.

OBJECTS OF THE INVENTION

An object of the present invention is to provide an improved reduction procedure for the preparation of donepezil hydrochloride, which is safe, industrially feasible, time efficient, cost effective and which provides donepezil hydrochloride in high yield and purity.

Another object of the invention is to minimize the partial debenzylation of donepezil to the impurity of formula (III) which forms during the reduction.

The invention is hereinafter detailed in details, no part of which may be construed as restrictive to the scope of the instant invention.

BRIEF SUMMARY OF THE INVENTION

According to a first aspect of the present invention, there is provided a process for preparing donepezil or a salt thereof, the process comprising reducing a 1-benzyl-4-[(5,6-dimethoxy-1-indanon-2-yl)methylene]pyridonium halide of formula II

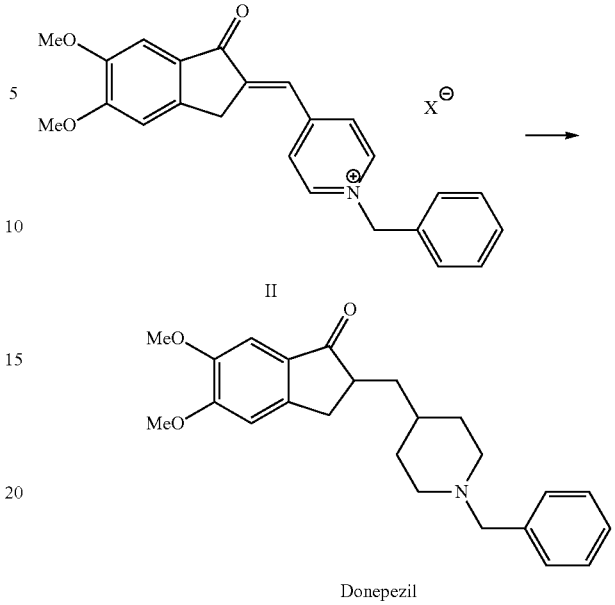

wherein X is bromide or chloride, in the presence of an ionic compound, a solvent, a catalyst and a source of hydrogen, to form donepezil and optionally converting the donepezil to the salt thereof. It will be appreciated that, compared to some of the multistep processes of the prior art, the process of the present invention is very simple, so is very suitable for industrial application.

In an embodiment, compound II is 1-benzyl-4-[(5,6-dimethoxy-1-indanon-2-yl)methylene]pyridonium bromide having the following structure.

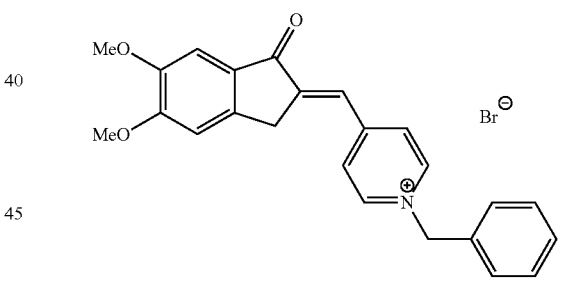

In an alternative embodiment, compound II is 1-benzyl-4-[(5,6-dimethoxy-1-indanon-2-yl)methylene]pyridonium chloride having the following structure.

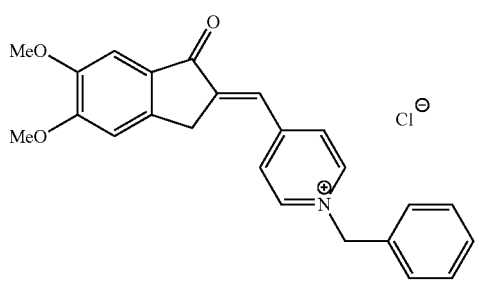 [SMILES: COc1cc2c(cc1OC)C(=O)/C(=C/c1cc[n+](Cc3ccccc3)cc1)C2 ; [Cl-]]

In an embodiment, the donepezil is converted to the salt thereof. Suitable salts are well known to those skilled in the art, and the process for preparing the salt would also be well known to those skilled in the art. Preferably, the process comprises converting donepezil to donepezil hydrochloride. The donepezil may be reacted with hydrochloric acid to form donepezil hydrochloride. The hydrochloric acid may be in the form of a methanolic solution. It will be appreciated that the process of the present invention may be a process for preparing a salt of donepezil, other than the hydrochloride salt. In which case, an acid other than hydrochloric acid would be present during the reaction. For example, formation of the hydrobromide salt would involve hydrobromic acid being present during the reduction.

The ionic compound may be an inorganic compound that is a solid at room temperature (20° C. to 25° C.). The ionic compound may also be a liquid, organic salt whose melting point is below 100° C. In an embodiment, the ionic compound is selected from the group consisting of a quaternary ammonium salt, a salt of an alkali metal, a salt of an alkaline earth metal, a formate, a perchlorate or mixtures thereof. The alkali metal may be sodium or potassium. The alkaline earth metal may be calcium. Typically, the ionic compound is selected from the group consisting of ammonium acetate, ammonium chloride-ammonium hydroxide, ammonium citrate, ammonium tartrate, calcium phosphate, citrate, phosphate, potassium phosphate, potassium acetate, potassium chloride, potassium citrate, sodium acetate, sodium chloride, triethylammonium formate, pyridinium formate, and sodium perchlorate. Preferably, the ionic compound is ammonium acetate.

The solvent may be an organic solvent, an aqueous solvent or mixtures thereof. The solvent may be a $C_1$ to $C_3$ alcohol. The solvent may be an ether. In an embodiment, the solvent is selected from the group consisting of methanol, ethanol, isopropyl alcohol, diethyl ether, diisopropyl ether, t-butyl methyl ether, tetrahydrofuran (THF), ethyl acetate, methylene chloride, ethylene chloride, rectified spirit, acetic acid, and mixtures thereof. Preferably, the solvent is a mixture of acetic acid, ethyl acetate, and rectified spirit.

In an embodiment, the catalyst is selected from the group consisting of palladium, palladium hydroxide, palladium on activated carbon, palladium on alumina, platinum, platinum on activated carbon, ruthenium, rhodium, and Raney nickel. Preferably, the catalyst is platinum on activated carbon.

Preferably, the process is a process for preparing donepezil hydrochloride, the ionic compound is ammonium acetate, the solvent is a mixture of acetic acid, ethyl acetate, and rectified spirit and the catalyst is platinum on activated carbon.

Suitably, the source of hydrogen is hydrogen gas. In an embodiment, the reduction reaction is carried out at a hydrogen gas pressure ranging from about 25 psi to about 80 psi, preferably from about 55 psi to about 60 psi.

Typically, the reduction reaction is carried out at a temperature ranging from about 10° C. to about 50° C., preferably from about 25° C. to about 30° C.

In an embodiment, the reduction reaction is carried out for a period of time ranging from about 2 hours to about 6 hours, preferably from about 3 hours to about 4 hours.

In an embodiment, the process of the present invention is a process for preparing donepezil free base, and the process further comprises converting the donepezil free base to a salt of donepezil following the reduction reaction.

The product of the reduction step may be purified for example by crystallization using a solvent or mixture of solvents.

According to another aspect of the present invention, there is provided donepezil hydrochloride having a purity of at least 98%, preferably at least 99%.

According to another aspect of the present invention, there is provided donepezil or a salt thereof, for example donepezil hydrochloride, prepared according to the process described above.

Preferably, the donepezil or salt thereof contains less than 0.1% of impurity of formula III,

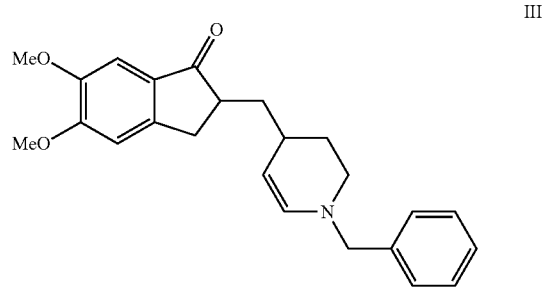 [SMILES: COc1cc2c(cc1OC)C(=O)C(CC1C=CN(Cc3ccccc3)CC1)C2]

preferably, less than 0.01% of impurity of formula III.

According to another aspect of the present invention, there is provided a pharmaceutical formulation comprising donepezil or a salt thereof as described above, together with one or more pharmaceutically acceptable excipients. Such excipients and formulations would be well known to those skilled in the art. The formulation may also include other active pharmaceutical ingredients.

According to another aspect of the present invention, there is provided the use of donepezil or a salt thereof as described above or a pharmaceutical formulation as described above, in medicine.

According to another aspect of the present invention, there is provided the use of donepezil or a salt thereof as described above or a pharmaceutical formulation as described above, in the treatment of a disease state prevented, ameliorated or eliminated by the administration of a cholinesterase inhibitor. In an embodiment, the disease is Alzheimer's disease.

According to another aspect of the present invention, there is provided a method of treating a disease state prevented, ameliorated or eliminated by the administration of a cholinesterase inhibitor in a patient in need of such treatment, which method comprises administering to the patient a therapeutically effective amount of donepezil or a salt thereof as described above. In an embodiment, the disease is Alzheimer's disease.

DETAILED DESCRIPTION OF THE INVENTION

The present invention relates to an improved reduction process for the synthesis of donepezil hydrochloride, which process is safe, industrially-feasible, time and cost effective and reduces the multiple steps of reduction during the preparation of donepezil hydrochloride compared to the prior art. In an embodiment, the process involves the use of the intermediate 1-benzyl-4-[(5,6-dimethoxy-1-indanon-2-yl)methylene]pyridonium bromide for the production of donepezil hydrochloride. In another embodiment, the process involves the use of the intermediate 1-benzyl-4-[(5,6-dimethoxy-1-indanon-2-yl)methylene]pyridonium chloride for the production of donepezil hydrochloride.

The term "donepezil" as used herein refers to all forms of donepezil inclusive of polymorphs thereof, for example, amorphous donepezil or crystalline donepezil. The donepezil may also be in the form of a hydrate, or a solvate thereof.

In an embodiment, the term "ionic compound" as used herein refers to an inert substance that minimizes changes in the pH of a solution. The ionic compound may thereby control the impurity formation during the reaction and may enhance the rate of reaction. The ionic compound may prevent changes in the acidity of a solution when an acid or base is added to the solution, or when the solution is diluted. Ionic compounds include ionic liquids and solids. While ionic inorganic compounds are solids at room temperature, organic ionic liquids may be salts whose melting point are relatively low (below 100° C.).

These ionic compounds not only have the potential to increase chemical reactivity and thus lead to a more efficient process, they are also non-flammable and are less toxic than conventional solvents due to their low vapor pressure.

It has been found that the yield of donepezil hydrochloride is substantially increased by using the process of the present invention, as a number of impurities formed are reduced due to the modified reduction step, thus the reaction becomes simpler and more easily achievable on an industrial scale.

In an embodiment, the overall scheme of reactions followed in the present invention is depicted below:

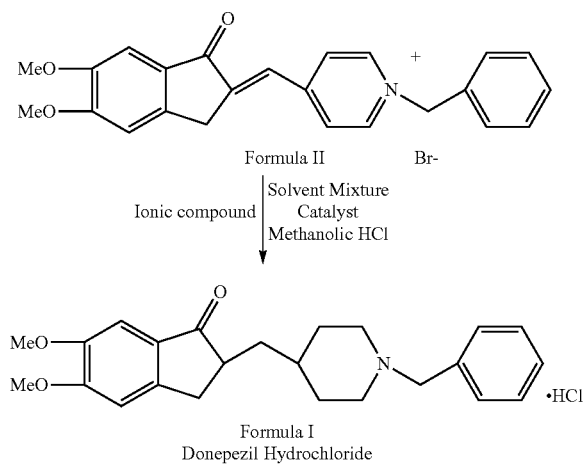

According to the invention, there is provided a process for the preparation of donepezil hydrochloride, comprising: catalytic hydrogenation of 1-benzyl-4-[(5,6-dimethoxy-1-indanon-2-yl)methylene]pyridonium bromide or chloride in the presence of an ionic compound and suitably using an organic solvent, or an aqueous solvents or mixtures thereof.

The ionic compound for use in a process according to the present invention may be selected from the group consisting of ammonium acetate, ammonium chloride-ammonium hydroxide, ammonium citrate, ammonium tartrate, calcium phosphate, citrate, phosphate, potassium phosphate, potassium acetate, potassium chloride, potassium citrate, sodium acetate, sodium chloride, triethylammonium formate, pyridinium formate, sodium perchlorate, and triethylammonium formate. The ionic compound may be used alone or in combination with other ionic compounds known to a person skilled in the art. A preferred ionic compound is ammonium acetate. Ammonium acetate may be added to maintain the pH of the reaction mixture thereby making the reaction faster and reducing the formation of the impurity of formula III.

A preferred catalyst for use in a process according to the present invention may be selected from the group consisting of palladium, palladium hydroxide, palladium on activated carbon, palladium on alumina, platinum, platinum on activated carbon, ruthenium, rhodium, and Raney nickel. In the process of the present invention, platinum on activated carbon is the most preferred catalyst. A combination of catalysts may also be used.

In an embodiment, the solvent is selected from the group consisting of methanol, ethanol, isopropyl alcohol, diethyl ether, diisopropyl ether, t-butyl methyl ether, tetrahydrofuran (THF), ethyl acetate, methylene chloride, ethylene chloride, rectified spirit, acetic acid, or mixtures thereof. Suitably, the solvent is a mixture of solvents. Preferably, the solvent is a mixture of acetic acid, ethyl acetate, and rectified spirit. As used herein, rectified spirit refers to ethanol which has been denatured by means of 5% methanol.

The reduction reaction is preferably carried out at a hydrogen gas pressure ranging from about 25 to about 80 psi, more preferably from about 55 to about 60 psi. The reduction reaction is preferably carried out at a temperature ranging from about 10 to about 50° C., more preferably about 25 to about 30° C. The reduction reaction is preferably carried out for a period of time ranging from about 2 to about 6 hours, more preferably about 3 to about 4 hours. These conditions are to be contrasted with the high pressure of 10 bar and high temperature of 70-95° C. as reported in the prior art; thus the present invention reduces reaction time, minimizes impurity levels and subsequently increases the yield.

It has been observed that donepezil of formula I obtained by the process of the present invention is highly pure. The term "highly pure" as used herein means a compound having HPLC purity of at least 98%, preferably at least 99%, typically around 99.8%. Preferably, donepezil obtained by following the process of the present invention is substantially free of the impurity of formula (III). The term "substantially free" as used herein means the donepezil product contains an amount of impurity of formula (III) less than 0.1%, preferably less than 0.05% and more preferably less than 0.01%.

Donepezil obtained by following the process of the present invention may be further purified, for example, by crystallization using a solvent or mixture of solvents to obtain donepezil in high purity and high yield. Donepezil obtained as a free base may be further converted to pharmaceutically acceptable salts.

The process is safe, simple, and easy as compared to those processes disclosed in the prior art. In an embodiment, the process uses a solvent comprising a mixture of acetic acid, ethyl acetate, and rectified spirit and this makes the process industrially and commercially viable. Further, in a preferred embodiment, the product obtained by following the process of the present invention, has a purity of at least 99.8% and contains less than 0.01% of impurity of formula (III).

The present invention also provides a method of treating a disease state prevented, ameliorated or eliminated by the administration of a cholinesterase inhibitor in a patient in need of such treatment, which method comprises administering to the patient a therapeutically effective amount of donepezil, or a pharmaceutically acceptable salt thereof, prepared according to the present invention, substantially as hereinbefore described.

While the present invention has been described in terms of its specific embodiments, certain modifications and equivalents will be apparent to those skilled in the art and are intended to be included within the scope of the present invention.

EXAMPLES

The invention is explained in more detail in the following working example. The example, which illustrates the method of the present invention, has a purely illustrative character and does not limit the extent of the invention in any respect.

Example 1

A solution of 1-benzyl-4-[(5,6-dimethoxy-1-indanon-2-yl)methylene]pyridonium bromide (20 kg) and ammonium acetate (2 kg) in ethyl acetate (450 lt) was charged into a hydrogenator. Then acetic acid (22 kg) and rectified spirit (100 lt) were added. A catalyst slurry (prepared separately by slurrying platinum on carbon (4 kg; 10% w/w) in water (6.6 lt) and acetic acid (78 kg)) was charged to the hydrogenator.

The reaction mass was hydrogenated by applying a hydrogen pressure of 55-60 psi at 25-30° C. and was maintained for 4 hours. After completion of the reaction, the reaction mass was filtered. The catalyst was washed with a mixture of rectified spirit (180 lt) and water (100 lt).

The combined clear filtrate was distilled off below 45° C. to remove solvents. The residue obtained was stirred with water (100 lt) and the pH of the reaction mass was adjusted to 7.5-8.0 using liquor ammonia at 25-30° C.

The solid was extracted with ethyl acetate (200 lt×3). The ethyl acetate layer was dried over sodium sulphate (10 kg) and distilled under reduced pressure below 45° C. To the residue, methanol (50 lt) was charged and distillation continued to remove traces of ethyl acetate below 45° C. To the residue, methanol (10 lt) was charged, the reaction mass cooled to 15-20° C. The pH of the reaction mass was adjusted to 2.0-2.5 using methanolic hydrochloric acid. To this solution, diisopropylether (80 lt) was added, the reaction mass chilled to 0-5° C. and the solids filtered.

The solid was purified by dissolving in a mixture of methanol (80 lt) and dichloromethane (25 lt) and precipitated by adding diisopropylether (150 lt) at 25-30° C., and stirred for 1 hour. The solid obtained was filtered and dried at 30-35° C. The solid was recrystallized from a mixture of methanol (15 lt) and diisopropylether (150 lt) to obtain donepezil hydrochloride.

Yield: ~14.0 kg (75%) HPLC purity >99.5%

Example 2

A solution of 1-benzyl-4-[(5,6-dimethoxy-1-indanon-2-yl)methylene]pyridonium bromide (10 kg) and 1-allylpyridinium bromide (2.65 kg) in ethyl acetate (225 lt) were charged into a hydrogenator. Then acetic acid (11 kg) and rectified spirit (50 lt) were added. A catalyst slurry (prepared separately by slurrying platinum on carbon (2 kg; 10% w/w) in water (3.3 lt) and acetic acid (39 kg)) was charged to the hydrogenator.

The reaction mass was hydrogenated by applying hydrogen pressure of 55-60 psi at 25-30° C. and was maintained for 4 hours. After completion of the reaction, the reaction mass was filtered. The catalyst was washed with a mixture of rectified spirit (90 lt) and water (50 lt).

The combined clear filtrate was distilled off below 45° C. to remove solvents. The residue obtained was stirred with water (50 lt) and the pH of the reaction mass was adjusted to 7.5-8.0 using liquor ammonia at 25-30° C.

The solid was extracted with ethyl acetate (100 lt×3). The ethyl acetate layer was dried over sodium sulphate (5 kg) and distilled under reduced pressure below 45° C. To the residue, methanol (25 lt) was charged and distillation continued to remove traces of ethyl acetate below 45° C. To the residue, methanol (5 lt) was charged, the reaction mass cooled to 15-20° C. The pH of the reaction mass was adjusted to 2.0-2.5 using methanolic hydrochloric acid. To this solution, diisopropylether (40 lt) was added, the reaction mass chilled to 0-5° C. and the solids filtered.

The solid was purified by dissolving in a mixture of methanol (40 lt) and dichloromethane (12.5 lt) and precipitated by adding diisopropylether (75 lt) at 25-30° C., and stirred for 1 hour. The solid obtained was filtered and dried at 30-35° C. The solid was recrystallized from a mixture of methanol (7.5 lt) and diisopropylether (75 lt) to obtain donepezil hydrochloride.

Yield: ~7.1 kg (77.42%) HPLC purity >99.5%

It will be appreciated that the invention may be modified within the scope of the appended claims.

The purity and impurity figures given in this specification are provided on a weight % basis.

The invention claimed is:

1. A process for preparing donepezil or a salt thereof, the process comprising reducing a 1-benzyl-4-[(5,6-dimethoxy-1-indanon-2-yl)methylene]pyridonium halide of formula II

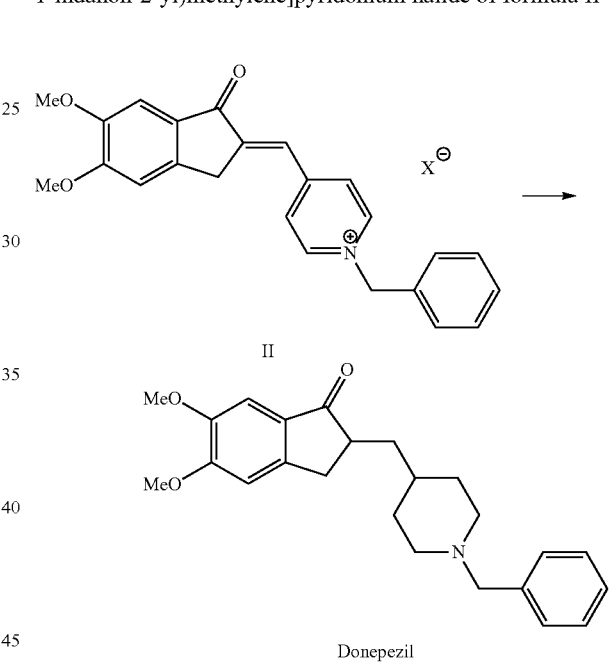

Donepezil wherein X⁻ is chloride or bromide, in the presence of an ionic compound, a solvent, a catalyst and a source of hydrogen, to form donepezil and optionally converting donepezil to the salt thereof, and wherein the catalyst is selected from the group consisting of palladium, palladium hydroxide, palladium on activated carbon, palladium on alumina, platinum, platinum on activated carbon, ruthenium, rhodium, and Raney nickel, wherein the ionic compound is ammonium acetate.

2. The process according to claim 1, wherein the donepezil is converted to a salt thereof.

3. The process according to claim 1, wherein the donepezil is converted to donepezil hydrochloride by reaction of donepezil with hydrochloric acid.

4. The process according to claim 3, wherein the hydrochloric acid is in the form of a methanolic solution.

5. The process according to claim 1, wherein the solvent is selected from the group consisting of methanol, ethanol, isopropyl alcohol, diethyl ether, diisopropyl ether, t-butyl methyl ether, tetrahydrofuran (THF), ethyl acetate, methylene chloride, ethylene chloride, rectified spirit, acetic acid, and mixtures thereof.

6. The process according to claim 1, wherein the solvent is a mixture of acetic acid, ethyl acetate, and rectified spirit.

7. The process according to claim 1, wherein the catalyst is platinum on activated carbon.

8. The process according to claim 1, wherein the source of hydrogen is hydrogen gas.

9. The process according to claim 8, wherein the reduction reaction is carried out at a hydrogen gas pressure ranging from about 25 psi to about 80 psi.

10. The process according to claim 9, wherein the reduction reaction is carried out at a hydrogen gas pressure ranging from about 55 psi to about 60 psi.

11. The process according to claim 1, wherein the reduction reaction is carried out at a temperature ranging from about 10° C. to about 50° C.

12. The process according to claim 1, wherein the reduction reaction is carried out at a temperature ranging about 25° C. to about 30° C.

13. The process according to claim 1, wherein the reduction reaction is carried out for a period of time ranging from about 2 hours to about 6 hours.

14. The process according to claim 1, wherein the reduction reaction is carried out for a period of time ranging from about 3 hours to about 4 hours.

15. The process according to claim 1, wherein the process is a process for preparing donepezil free base, and the process further comprises converting the donepezil free base to a salt of donepezil following the reduction reaction.

16. The process according to claim 1, wherein the product of the reduction step is purified by crystallization using a solvent or mixture of solvents.

17. The process according to claim 1, wherein compound II is 1-benzyl-4-[(5,6-dimethoxy-1-indanon-2-yl)methylene] pyridonium bromide having the following structure,

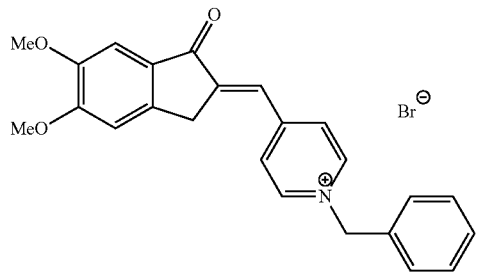

or 1-benzyl-4-[(5,6-dimethoxy-1-indanon-2-yl)methylene] pyridonium chloride having the following structure

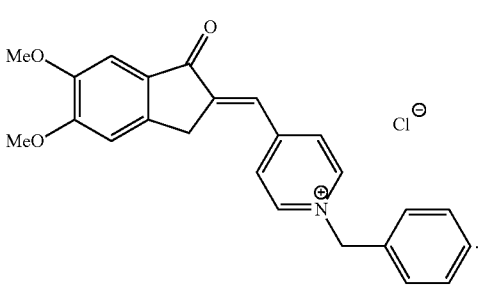 [SMILES: COc1cc2c(cc1OC)C(=O)/C(=C/c1cc[n+](Cc3ccccc3)cc1)C2 ; [Cl-]]

* * * * *